(12) United States Patent
Walter et al.

(10) Patent No.: US 8,105,684 B2
(45) Date of Patent: Jan. 31, 2012

(54) SUBSTRATE, METHOD FOR THE PRODUCTION THEREOF AND USE THEREOF IN ORDER TO FORM CULTURES OF ORGANIC CELLS

(75) Inventors: Alexander Walter, Munich (DE); Udo Leuschner, Regensburg (DE); Erich Wintermantel, Freising (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 917 days.

(21) Appl. No.: 11/660,126

(22) PCT Filed: Aug. 17, 2005

(86) PCT No.: PCT/EP2005/008927
§ 371 (c)(1),
(2), (4) Date: Aug. 2, 2007

(87) PCT Pub. No.: WO2006/018298
PCT Pub. Date: Feb. 23, 2006

(65) Prior Publication Data
US 2008/0107853 A1 May 8, 2008

(30) Foreign Application Priority Data
Aug. 17, 2004 (DE) .......................... 10 2004 039 762

(51) Int. Cl.
*B32B 3/26* (2006.01)
*B05D 5/00* (2006.01)
(52) U.S. Cl. ............... 428/315.7; 428/305.4; 428/314.2; 428/314.4; 428/314.8; 428/315.5; 428/319.3; 623/23.51; 623/23.58; 427/243

(58) Field of Classification Search ............... 428/315.5, 428/315.7, 314.2, 314.4, 314.8, 305.5, 319.3; 427/243; 623/23.51, 23.58
See application file for complete search history.

(56) References Cited

U.S. PATENT DOCUMENTS

| | | | |
|---|---|---|---|
| 6,337,198 B1* | 1/2002 | Levene et al. ................. | 435/174 |
| 2003/0065400 A1* | 4/2003 | Beam et al. ................. | 623/23.51 |
| 2003/0072790 A1* | 4/2003 | Tsai et al. .................... | 424/443 |
| 2003/0180942 A1 | 9/2003 | Van Der Merwe et al. | |
| 2005/0043816 A1* | 2/2005 | Datta et al. ................. | 623/23.61 |

FOREIGN PATENT DOCUMENTS

| | | |
|---|---|---|
| DE | 103 26 744 A1 | 1/2005 |
| EP | 0 420 171 A1 | 4/1991 |
| JP | 06133760 A | 5/1994 |

* cited by examiner

*Primary Examiner* — Hai Vo
(74) *Attorney, Agent, or Firm* — Edwards Wildman Palmer LLP; Scott D. Wofsy; Gabriel J. McCool

(57) ABSTRACT

A substrate for forming cultures of organic cells, comprising the following a spatial body,
the cross section of the body comprises a plurality of at least first pores, wherein the pre size of a majority thereof is =1000 μm, preferably 10-500 μm, more preferably 10-200 μm, most preferably 10-100 μm t;
the first pores are fluidically connected to each other:
at least the first pores whose pore size is in the region of 500 μm have a cell-growth promoting property and at least one part of the first pores arranged close to at least one free surface of the body are open towards the outer environment. Preferably, the substrate is an open-pored foam material body made of a synthetic material. The substrate enables spatial cell cultures to be formed.

17 Claims, 1 Drawing Sheet

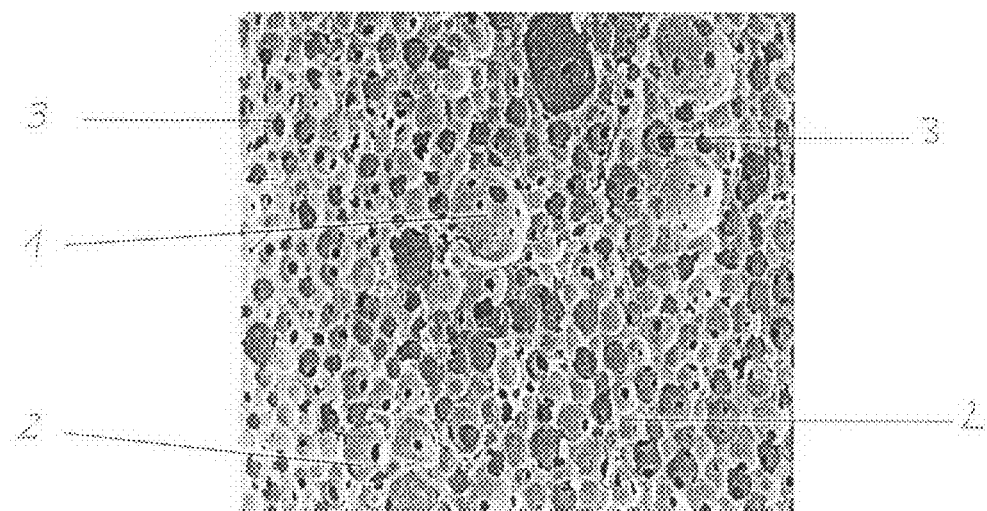

SUBSTRATE, METHOD FOR THE PRODUCTION THEREOF AND USE THEREOF IN ORDER TO FORM CULTURES OF ORGANIC CELLS

The invention relates to a substrate, a method for the production thereof and use thereof in order to form cultures of organic cells.

A conventional practice for multiplying organic cells such as are required for investigations of the most diverse type in the medical or non-medical fields, envisages the creation of a cell culture on flat, possibly protein coated cover glasses in so-called Petri dishes. A cell culture in the form of a mono layer thereby develops on the cover glasses. It has already been proposed (WO 97/08291) that a growth vessel be provided with a rough or uneven growth surface so that depressions of up to 1 mm will be formed therein. A cell growth process producing a greater yield at higher speed is thereby attainable. Micro-surface-structured cell growth vessels whose surfaces have regularly or irregularly arranged bumps of less than 100 μm are known from WO 99/45096 for example. The factor common to these known manners of procedure is that the cell culture obtained therefrom is characterized by an essentially laminar configuration having only a small elongation in the thickness direction.

In contrast thereto, the object of the invention is to provide a substrate for forming cultures having basically unlimited spatial boundaries as well as to provide a method for the production thereof.

In accordance with one aspect of the invention, there is provided a substrate which comprises the following features: A spatial body; the cross section of the body includes a plurality of at least first pores; of which the majority has a pore-size $\leq 1000$ μm, preferably of 10 to 500 μm, more preferably of 10 to 200 μm, and most preferably of 10 to 100 μm; the first pores have a fluidic connection to one another; at least those first pores having a pore-size within the range of 10 to 500 μm have a cell growth-promoting property; at least a part of the first pores located close to at least one free surface of the body are open to the outer environment.

A feature of the invention is that the substrate is designed to be in the form of a three-dimensional body having an open-pored cross sectional structure. In particular, the cross sectional structure is defined by first pores of a certain dimension (inside width) in which the first pores have a fluidic connection to one another and of which those that lie close to a free surface of the body are open to or open out into the outer environment. The term "inside width" or pore-size, respectively means the diameter of a circle having a surface area corresponding to the cross-sectional area having the largest surface area of all sectional planes of a pore.

The term "pores" as used here is not restricted to depressions or cavities in the surface but also embraces, in particular, cells or empty spaces having a regular or irregular peripheral configuration that are present in the interior of the substrate. The distribution of the pores over the cross section of the substrate may be uniform or non-uniform.

The cells of a cell suspension brought into contact with the free surface of a substrate according to the invention can grow into the pores so that the entire open-pore structure of the substrate is gradually occupied with cells and a spatial cell culture corresponding to the configuration of the substrate is formed. In accordance with the invention, the filling of the substrate with cells is promoted by virtue of at least those pores whose pore-size lies within a certain size-range of 10 μm to 500 μm exhibiting a cell growth-promoting property. It is self evident that any larger pores which may be present could likewise have this property.

The cell growth-promoting property can be the result of the walls of the pores exhibiting a hydrophilic property. To this end, an ionised gaseous medium can be caused to penetrate into the substrate in the course of a plasma treatment such as is in principle known to the skilled person so that a more detailed explanation thereof is unnecessary, in order to raise the surface energy at the inner surfaces of the pores to a suitable level, e.g. 60 mN/m. The gaseous medium may, for example, be ionised air which can be introduced into the pores under a suitable positive pressure, or $O_2N_2$. The latter is preferably caused to penetrate into the pores by means of a negative pressure effect. Because of the existing fluidic connection between the pores, the gas can be applied to the entire cross section of the substrate. The invention is not limited to the previously mentioned special gases. Other suitable gases could also be used if so desired.

An alternative manner of producing pores with a cell growth-promoting property envisages that the inner surfaces of the pores be subjected to a hydrophilic process by means of a coating process involving the application of a hydrophilic coating solution, e.g. polylysin, fibronectin, collagen, gelatine as well as a combination thereof. Such solutions are, in principle, likewise known to the skilled person. For more details thereof, reference can be made to e.g. Lindl, Zell- und Gewebekultur, Spectrum publishing house, Berlin, 2000, pages 33 et. seq. as well as E. Wintermantel, Medizintechnik mit biocompatiblen Werkstoffen und Verfahren, Springer publishing house, Berlin, 2002, pages 73 et. seq., these sources thereby being incorporated into the present disclosure.

A further alternative envisages the provision of a substrate consisting of a hydrophilic synthetic material which may, for example, be a copolymer with hydrophilic groups, e.g. polyether-polyurethane-hydrogel.

Furthermore, experiments that have been performed within the framework of the invention have shown that pores, which contain discontinuities such as corners, kinks, edgings, can hinder cell growth or lead to insufficient cells being filled in. In accordance with an embodiment of the invention, provision is therefore made for the walls of at least a majority of the first pores to be essentially continuously curved, i.e. the wall surface is essentially free of corners, kinks, edgings and the like so that the wall surface represents a continuum.

A preferred embodiment of the invention envisages that, in addition to the first pores, there be second pores which, however, do not provide for cell growth, but rather, serve for accommodating certain effective substances which can promote cell growth in the first pores or protect it from harmful effects. These effective substances, which may, for example, be cell nutriments, cell growth promoters, medicaments etc., can be passed on to the first pores by a diffusion process. In this case, the second pores can be closed. Or, the second pores have a fluidic connection to the adjacent first pores through passages of narrow width. These second pores have a pore-size which is substantially smaller than that of the first pores, preferably $\ll 10$ μm. At least one second pore is provided near or adjacent to a respective first pore of at least a plurality of such first pores.

Although the substrate is generally left as a mechanical support for the cell culture that is formed after the cells have grown therein, nevertheless provision may, in accordance with a further embodiment of the invention, also be made for the substrate to consist of a biologically degradable material.

Suitable materials are e.g. polylactic acid, polyglycol acid as well as the copolymers thereof.

Although a substrate comprising the pore structure in accordance with the invention could consist of other materials, e.g. a composite layered material (stacked structured layers with regular or irregularly arranged perforations), it is preferably an open-pored foamed material body formed of a suitable synthetic material such as thermoplastic polyurethane or polystyrene because of the production advantages arising from the use of an injection moulding process. Thereby, the body can be formed of any shape, e.g. plate-like or in the form of a cell culture vessel. Although open-pored, dimensionally stable foamed material bodies wherein the individual pores are connected with each other by passages of narrow width are known (DE 4 304 085 A), these foamed material bodies only serve as filters, insulating materials or lightweight construction materials. Furthermore, in the document a method for the production of an open-pored foamed material body is described with further details.

In accordance with another aspect of the invention, there is provided a method for the production of a substrate of the aforementioned type which is characterised in that, in a first step, an open-pored foamed material is formed which comprises a plurality of at least first pores of which the majority have a pore-size $\leq 1000$ µm, preferably of 10 to 500 µm, more preferably of 10 to 200 µm, and most preferably of 10 to 100 µm by a process of foaming a synthetic material, whereby the first pores have a fluidic connection to one another, and, in a second step, the foamed material is subjected to a hydrophilic treatment. Suitable hydrophilic treatments were described hereinabove; they can be used either alone or in combination.

EXAMPLE

A micro cross section of a cell growth substrate according to the invention in the form of an open-pored foamed material body of a polyurethane synthetic material is shown in the drawing.

As illustrated, the substrate comprises a plurality of pores wherein a cell growth can take place, whereby the pore-sizes thereof can vary but should however amount to $\leq 1000$ µm. The pore-size is subject to a statistical distribution. In the embodiment shown, a statistical minority of the pores 1 have a pore-size of e.g. 400-500 µm whereas the majority of the pores as indicated by 2 is substantially smaller and the size thereof amounts to e.g. only 10-100 µm. In the example shown, the proportion of the small pores 2 to the larger pores 1 is to between 80 and 90%. The large number of smaller pores 2 provided with a cell growth-promoting property is advantageous since a considerable enlargement of the surface area can thereby be obtained.

As can be seen, the overwhelming number of pores 1, 2 have walls which are free of kinks, sharp corners or edgings and therefore essentially represent a continuum.

Passages (shown in black) in the walls of the pores are indicated by 3 and these form a fluidic connection between neighbouring pores 1, 2.

The synthetic material may be a thermoplastic polyurethane which is foamed in an injection moulding process. A suitable foaming process is described in EP 952 908 B1 so that reference may be made thereto.

Not illustrated here, are second pores for accommodating certain effective substances of the aforementioned type provided in the interspaces between neighbouring pores 1, 2 or within these pores. To this end, capsules which contain the effective substance for example can be mixed with the thermoplastic raw material prior to the foaming process.

The invention claimed is:

1. A substrate comprising:
   a spatial body comprised of a single type of polymer material,
   the cross section of the body includes a plurality of at least first pores with a pore-size of less than or equal to 1000 µm and each having a substantially continuously smooth surface;
   all the first pores have a fluidic connection to one another;
   at least those first pores having a pore-size within the range of 10 to 500 µm have a cell growth-promoting property,
   at least a part of the first pores located close to at least one free surface of the body is open to the outer environment; and
   wherein said cross section further comprises second pores, wherein said second pores are closed, provided within the first pores, accommodate one or more effective substances for promoting or protecting cell growth, and do not provide for cell growth.

2. The substrate according to claim 1, wherein the cell growth-promoting property comprises a hydrophilic property of the walls of the pores.

3. The substrate according to claim 1, wherein the one or more effective substances are cell nutrients, cell growth promoters, or medicaments, and wherein said second pores have a pore-size which is less than 10 µm.

4. The substrate according to claim 1, wherein an exchange of fluid between the second pores with the neighbouring first pores is effected by a diffusion process.

5. The substrate according to claim 1, wherein the single type of polymer material is a synthetic material.

6. The substrate according to claim 5, wherein the single type of polymer material is a biologically degradable material.

7. The substrate according to claim 1, wherein the body is a plate.

8. The substrate according to claim 1, wherein the body is in the form of a cell culture vessel.

9. The substrate according to claim 1, wherein the first pores have a pore-size of 10 µM to 200 µM.

10. The substrate according to claim 1, wherein the first pores have a pore-size of 10 µM to 100 µM.

11. A method for producing the substrate of claim 1, comprising: foaming the single type of polymer material to form the spatial body, and subjecting the spatial body to a hydrophilic treatment.

12. A method according to claim 11, wherein the hydrophilic treatment comprises allowing an ionized gaseous medium to penetrate into the spatial body.

13. A method according to claim 11, wherein the hydrophilic treatment comprises providing the pore surfaces of the spatial body with a hydrophilic coating of a hydrophilic coating material.

14. A method according to claim 13, wherein the hydrophilic coating material is selected from the group consisting of polylysins, fibronectines, collagens, gelatines and combinations thereof.

15. A method according to claim 11, wherein the single type of polymer material comprises a copolymer.

16. A method according to claim 15, wherein the copolymer is a polyether polyurethane hydrogel.

17. A method of forming a culture of cells, comprising: contacting cells with the substrate of claim 1 and allowing for cell growth.

* * * * *